(12) United States Patent
Izumimoto et al.

(10) Patent No.: US 8,106,065 B2
(45) Date of Patent: Jan. 31, 2012

(54) ANTITUSSIVE AGENT

(75) Inventors: Naoki Izumimoto, Kamakura (JP); Koji Kawai, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 12/158,100

(22) PCT Filed: Dec. 15, 2006

(86) PCT No.: PCT/JP2006/325023
§ 371 (c)(1),
(2), (4) Date: Jun. 19, 2008

(87) PCT Pub. No.: WO2007/072749
PCT Pub. Date: Jun. 28, 2007

(65) Prior Publication Data
US 2009/0176818 A1 Jul. 9, 2009

(30) Foreign Application Priority Data

Dec. 21, 2005 (JP) .................................. 2005-367825

(51) Int. Cl.
*A61K 31/4748* (2006.01)
*A61P 11/14* (2006.01)
*C07D 489/02* (2006.01)
(52) U.S. Cl. .......................................... 514/289; 546/74
(58) Field of Classification Search .................. 514/289; 546/74
See application file for complete search history.

(56) References Cited

U.S. PATENT DOCUMENTS

| | | | | |
|---|---|---|---|---|
| 3,108,041 A | * | 10/1963 | Weiner | 514/282 |
| 6,174,891 B1 | | 1/2001 | Nagase et al. | |
| 7,320,984 B2 | * | 1/2008 | Izumimoto et al. | 514/282 |

FOREIGN PATENT DOCUMENTS

| | | |
|---|---|---|
| EP | 1 820 505 A1 | 8/2007 |
| JP | 41 018823 | 10/1966 |
| WO | WO-95/03308 A1 | 2/1995 |
| WO | WO-98/23290 A1 | 6/1998 |
| WO | WO-2005/094826 A1 | 10/2005 |
| WO | WO-2006/049248 A1 | 5/2006 |

* cited by examiner

*Primary Examiner* — San-Ming Hui
*Assistant Examiner* — Kathrien Cruz
(74) *Attorney, Agent, or Firm* — Birch, Stewart, Kolasch and Birch, LLP

(57) ABSTRACT

An antitussive, which can be used for therapy or prophylaxis of coughing, is disclosed. The antitussive comprises as an effective ingredient a morphinan derivative having a nitrogen-containing cyclic substituent or a pharmaceutically acceptable acid addition salt thereof, having a specific structure, such as the compound below [N-(17-cyclopeopylmethyl-4,5α-epoxy-3,14-dihydroxy-morphinan-6β-yl)-3,4,5,6-tetrahydrophthalimide]. The antitussive has an excellent therapeutic or prophylactic effect against coughing and the side effects thereof are small.

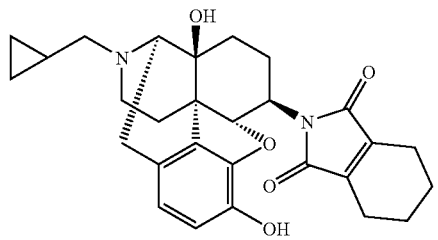

1 Claim, No Drawings

ANTITUSSIVE AGENT

TECHNICAL FIELD

The present invention relates to an antitussive comprising as an effective ingredient a morphinan derivative having a nitrogen-containing cyclic substituent or a pharmaceutically acceptable acid addition salt thereof, which is useful for therapy or prophylaxis of coughing.

BACKGROUND ART

Antitussives are widely used for therapy of coughing associated with respiratory disorders such as cold (common cold syndrome), bronchitis and pneumonia. Antitussives can be classified into groups of central antitussives, which act on the cough center, and peripheral antitussives. The majority of antitussives presently used are the central antitussives, and they can further be classified into nonnarcotic antitussives and narcotic antitussives.

As nonnarcotic antitussives, tipepidine hibenzate, dextromethorphan hydrobromide and the like are frequently used. However, they often cause drowsiness, dizziness, headache or the like by acting on other targets than the cough center and have fewer efficacies than narcotic ones, and thus may not induce a sufficient antitussive effect.

As narcotic antitussives, codeine phosphate, dihydrocodeine phosphate and the like are commonly used and whereby relatively higher efficacy can be expected. However, they also accompany side effects such as constipation, nausea, vomiting, headache and drowsiness, and cause tolerance, dependence and drug abuse are caused, which are also problematic.

Although codeine phosphate and dihydrocodeine phosphate have the morphinan skeleton, the 6-position thereof is substituted with a hydroxy group and differ from the compound according to the present invention, which has a nitrogen-containing cyclic substituent at the 6-position thereof. Among the morphinan compounds that have a nitrogen-containing cyclic substituent at the 6-positions thereof, it has already been reported that cyclic amino-substituted compounds have antitussive effects (Patent Literature 1, 2 and 3). In addition, chemical structures of some compounds among morphinan compounds, having cyclic imido-substituents at the 6-position thereof, are disclosed, although the antitussive effect of which is not directly indicated (Non-Patent Literature 1, 2 and 3). On the other hand, it has been disclosed that the compound according to the present invention has a therapeutic effect on frequent urination and urinary incontinence (Patent Literature 4), pruritus (Patent Literature 5), and pain (Patent Literature 6) (the therapeutic use against pain was disclosed after the priority date of the present application).

However, none of these disclosures infer that the compounds according to the present invention have a remarkable antitussive effect with few side effects, so that they may be useful as antitussives.

Patent Literature 1: Japanese Patent Publication (Kokoku) No. 41-18824

Patent Literature 2: Japanese Patent Publication (Kokoku) No. 41-18826

Patent Literature 3: International Publication WO 95/03308

Patent Literature 4: International Publication WO 2004/033457 (European Publication EP1555266)

Patent Literature 5: International Publication WO 2005/094826

Patent Literature 6: International Publication WO 2006/049248

Non-Patent Literature 1: Simon C. et. al., Tetrahedron, 50, 9757-9768, 1994.

Non-Patent Literature 2: Sayre L. M. et. al., J. Med. Chem., 27, 1325-1335, 1984.

Non-Patent Literature 3: Simon C. et. al., Synth. Commun., 22, 913-921, 1992.

DISCLOSURE OF THE INVENTION

Problems which the Invention Tries to Solve

An object of the present invention is to provide an antitussive comprising as an effective ingredient a morphinan derivative having a nitrogen-containing cyclic substituent or a pharmaceutically acceptable acid addition salt thereof, which is useful for therapy or prophylaxis of coughing.

Means for Solving Problem

The present inventors intensively studied for attaining the above-described object to discover that the compounds having a nitrogen-containing cyclic substituent on a specific position of the morphinan structure have excellent antitussive effect, and the side effects thereof are small, thereby completing the present invention.

That is, the present invention provides an antitussive comprising as an effective ingredient a morphinan derivative having a nitrogen-containing cyclic substituent of the Formula (I):

[wherein $R^1$ represents hydrogen, $C_1$-$C_5$ alkyl, $C_4$-$C_7$ cycloalkylalkyl, $C_5$-$C_9$ cycloalkenylalkyl, $C_6$-$C_{12}$ aryl, $C_7$-$C_{13}$ aralkyl, $C_3$-$C_7$ alkenyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5);

$R^2$ and $R^3$ represent independently hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy;

—X— represents $C_2$-$C_7$ alkylene, alkenylene or alkynylene (one or more of the carbon atoms therein may be replaced by (a) nitrogen, oxygen and/or sulfur atom(s)) constituting a part of the ring structure;

Y represents valence bond, —C(=O)—, —C(=S)—, —S(O)—, —S(O$_2$)—, —N(—R$^4$)—, —C(=O)—N(—R$^4$)—, or, —C(=S)—N(—R$^4$)—;

$R^4$ represents hydrogen or $C_1$-$C_5$ alkyl;

k represents an integer of 1 to 8;

$R^5$(s) represent(s) (a) substituent(s) in the number of k on the ring structure, which independently represent(s) fluorine, chlorine, bromine, iodine, nitro, $C_1$-$C_8$ alkyl, $C_1$-$C_5$ alkylidene, $C_7$-$C_{13}$ cycloalkylalkyl, $C_7$-$C_{13}$ cycloalkylalkylidene, $C_6$-$C_{12}$ aryl, $C_7$-$C_{13}$ aralkyl, $C_7$-$C_{13}$ aralkylidene, $C_6$-$C_{12}$ aryloxy, trifluoromethyl, trifluoromethoxy, cyano, isothiocyanato, $(CH_2)_pSR^7$, $(CH_2)_pS(O)R^7$, $(CH_2)_pS(O_2)R^7$, $(CH_2)_pOR^7$, $(CH_2)_pC(=O)R^7$, $(CH_2)_pOC(=O)R^7$, $(CH_2)_pCO_2R^7$, $(CH_2)_pS(O)NR^8R^9$, $(CH_2)_pS(O_2)NR^8R^9$, $(CH_2)_pC(=O)NR^8R^9$, $(CH_2)_pNR^8R^9$, $(CH_2)_pN(R^8)C(=O)R^9$, or $(CH_2)_pN(R^8)S(O_2)R^9$, or among the $R^5$s in the number of k, two $R^5$s bound to the same carbon atom or to the same sulfur atom together represent one oxygen atom to form carbon-yl or sulfoxide, two $R^5$s bound to the same carbon atom together represent one sulfur atom to form thiocarbonyl (with the proviso that, in case where Y is valence bond, thus formed carbonyl does not directly bind to a nitrogen atom which is bound to morphinan skeleton), four $R^5$s bound to the same sulfur atom together represent two oxygen atoms to form sulfone, or among the $R^5$s in the number of k, two $R^5$s bound to adjacent carbon atoms, respectively, together form benzo, pyrido, naphtho, cyclopropano, cyclobutano, cyclopentano, cyclopenteno, cyclohexano, cyclohexeno, cycloheptano or cyclohepteno, each of the above-mentioned groups from benzo to cyclohepteno being unsubstituted or substituted with 1 or more $R^6$s, wherein $R^6(s)$ independently represent(s) fluorine, chlorine, bromine, iodine, nitro, $C_1$-$C_5$ alkyl, $C_7$-$C_{13}$ aralkyl, trifluoromethyl, trifluoromethoxy, cyano, $C_6$-$C_{12}$ aryl, isothiocyanato, $(CH_2)_pSR^7$, $(CH_2)_pS(O)R^7$, $(CH_2)_pS(O_2)R^7$, $(CH_2)_pOR^7$, $(CH_2)_pC(=O)R^7$, $(CH_2)_pOC(=O)R^7$, $(CH_2)_pCO_2R^7$, $(CH_2)_pS(O)NR^8R^9$, $(CH_2)_pS(O_2)NR^8R^9$, $(CH_2)_pC(O)NR^8R^9$, $(CH_2)_pNR^8R^9$, $(CH_2)_pN(R^8)C(=O)R^9$, or $(CH_2)_pN(R^8)S(O_2)R^9$;

p represents an integer of 0 to 5;

$R^7$, $R^8$ and $R^9$ represent independently hydrogen, $C_1$-$C_5$ alkyl, $C_3$-$C_7$ alkenyl, $C_6$-$C_{12}$ aryl or $C_7$-$C_{13}$ aralkyl;

$R^{10}$ represents hydrogen, $C_1$-$C_5$ alkyl, $C_2$-$C_5$ alkenyl, $C_7$-$C_{13}$ aralkyl, $(CH_2)_pOR^7$ or $(CH_2)_pCO_2R^7$ (wherein p and $R^7$ represent the same meanings as described above);

$R^{11}$ and $R^{12}$ are bound to form —O—, —S— or —$CH_2$—, or $R^{11}$ represents hydrogen and $R^{12}$ represents hydrogen, hydroxy, $C_1$-$C_5$ alkoxy or $C_1$-$C_5$ alkanoyloxy; and $R^{13}$ and $R^{14}$ together represent oxo, or $R^{13}$ represents hydrogen and $R^{14}$ represents hydrogen, hydroxy, $C_1$-$C_5$ alkoxy or $C_1$-$C_5$ alkanoyloxy; and the Formula (I) includes (+), (−) and (±) isomers]

or a pharmaceutically acceptable acid addition salt thereof. The present invention also provides a use of the morphinan derivative having the nitrogen-containing cyclic substituent or the pharmaceutically acceptable acid addition salt thereof for the production of an antitussive. The present invention further provides a method for suppressing cough, comprising administering an effective amount of the morphinan derivative having the nitrogen-containing cyclic substituent or the pharmaceutically acceptable acid addition salt thereof.

Effects of the Invention

The antitussive according to the present invention has an excellent therapeutic or prophylactic effect against coughing and the side effects thereof are small.

BEST MODE FOR CARRYING OUT THE INVENTION

As described above, the antitussive according to the present invention comprises as an effective ingredient the morphinan derivative having a nitrogen-containing cyclic substituent, represented by the above-described Formula (I) or a pharmaceutically acceptable acid addition salt thereof.

Among the compounds represented by Formula (I), as for $R^{13}$ and $R^{14}$, those wherein $R^{13}$ and $R^{14}$ together represent oxo or $R^{13}$ is hydrogen and $R^{14}$ is hydrogen or hydroxy are preferred, and those wherein both $R^{13}$ and $R^{14}$ are hydrogen, that is, unsubstituted compounds, are preferred.

Those wherein Y represents valence bond or —C(=O)— are especially preferred.

$R^1$ is preferably hydrogen, $C_4$-$C_7$ cycloalkylalkyl, $C_6$-$C_8$ cycloalkenylalkyl, $C_6$-$C_{12}$ aryl or $C_3$-$C_7$ alkenyl, particularly, hydrogen, cyclopropylmethyl, 2-cyclopropylethyl, 3-cyclopropylpropyl, 4-cyclopropylbutyl, cyclobutylmethyl, cyclopentylmethyl, cyclohexylmethyl, cyclobutenylmethyl, 2-cyclobutenylethyl, 3-cyclobutenylpropyl, phenyl, naphthyl, allyl or prenyl. Among these, hydrogen, cyclopropylmethyl, cyclobutylmethyl, cyclopentylmethyl, cyclohexylmethyl, allyl and prenyl are preferred, and hydrogen, cyclopropylmethyl, cyclobutylmethyl and allyl are especially preferred.

$R^2$ and $R^3$ are preferably hydrogen, hydroxy, methoxy, ethoxy, allyloxy, benzyloxy, acetoxy or propionoxy, more preferably, hydrogen, hydroxy, methoxy or acetoxy.

—X— is preferably $C_2$-$C_4$ allylene or alkenylene (one carbon atom therein may be replaced by a sulfur atom) constituting a part of the ring stricture, more preferably, ethylene (—$CH_2$—$CH_2$—), vinylene (—CH=CH—), propenylene (—$CH_2$—CH=CH—) or —S—CH=CH—.

k is preferably an integer of 2 to 8, more preferably 2 to 6, still more preferably 2 or 6.

It is preferred that $R^5$ be $C_1$-$C_5$ alkyl, $C_1$-$C_5$ alkylidene, $C_7$-$C_{13}$ cycloalkylalkyl, $C_7$-$C_{13}$ aralkyl or $C_7$-$C_{13}$ aralkylidene, or that two $R^5$s bound to adjacent carbon atoms, respectively, together form benzo, pyrido, naphtho, cyclopropano, cyclobutano, cyclopentano, cyclopenten-o, cyclohexano, cyclohexeno, cycloheptano or cyclohepteno, each of the above-mentioned groups from benzo to cyclohepteno being unsubstituted or substituted with 1 or more $R^6$s. In addition, the cases where X is —S—CH=CH—, and among the $R^5$s in the number of k, four $R^5$s bound to the same sulfur atom together represent two oxygen atoms to form sulfone are preferred. It is more preferred that $R^5$ be methyl, ethyl, ethylidene, propyl, propylidene, butyl, butylidene, benzyl, benzylidene, phenethyl, phenethylidene or cyclohexylmethyl, or that two $R^5$s bound to adjacent carbon atoms, respectively, together form benzo or cyclohexeno, which benzo or cyclohexeno is unsubstituted or substituted with 1 or more $R^6$s, more preferably that two $R^5$s bound to adjacent carbon atoms, respectively, together form benzo or cyclohexeno, which benzo or cyclohexeno is unsubstituted or substituted with 1 or more (particularly 1 to 4) $R^6$s. In addition, the cases where X is —S—CH=CH—, and among the $R^4$s in the number of k, four $R^4$s bound to the same sulfur atom together represent two oxygen atoms to form sulfone are also especially preferred. Although unsubstituted benzo or unsubstituted cyclohexeno is also preferred, the substituent(s) $R^6(s)$ is(are) preferably and independently fluorine, chlorine, bromine, iodine, nitro, methyl, ethyl, propyl, benzyl, hydroxy, methoxy, ethoxy, trifluoromethyl, trifluoromethoxy, cyano, phenyl, isothiocyanato, mercapto, methylthio, methylsulfinyl, methylsulfonyl, hydroxymethyl, hydroxyethyl, methoxymethyl, ethoxymethyl, methoxyethyl, phenoxy, acetoxy, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl, amino, acetamino, acetaminomethyl or methansulfonamide.

$R^{10}$ is preferably hydrogen, $C_1$-$C_5$ alkyl, allyl or benzyl, more preferably hydrogen or methyl.

It is preferred that $R^{11}$ and $R^{12}$ be bound to form —O—, or that $R^{11}$ be hydrogen and $R^{12}$ be hydrogen, hydroxy or methoxy, and more preferred that $R^{11}$ and $R^{12}$ be bound to form —O—.

Preferred examples of the pharmaceutically acceptable acid addition salts include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are preferred, but the acid addition salt is not restricted thereto.

Among the compounds of the Formula (I) according to the present invention, specific examples of those wherein —X— is vinylene (—CH=CH—); Y is —C(=O)—; two $R^5$s bound to adjacent carbon atoms together form benzo or cyclohexeno, which benzo or cyclohexeno is unsubstituted or substituted with one or more substituents $R^6$(s); $R^{10}$, $R^{13}$ and $R^{14}$ are hydrogen; $R^{11}$ and $R^{12}$ are bound to form —O—, that is, those represented by the Formula (Ia) or (Ia') below, as well as those wherein —X— is —S—CH=CH—: Y is valence bond; four $R^5$s bound to the sulfur atom together represent two oxygen atoms to form sulfone; two $R^5$s bound to adjacent carbon atoms together form benzo which is unsubstituted or substituted with one or more substituents $R^6$(s); $R^{10}$, $R^{13}$ and $R^{14}$ are hydrogen; and $R^{11}$ and $R^{12}$ are bound to form —O—, that is, those represented by the Formula (Ia") are shown in Table 1. In the tables described below, CPM means cyclopropylmethyl; the number attached to the substituent $R^6$ is the position of the substituent on the benzene ring in the phthalimide structure, on the cyclohexene ring in the tetrahydropthalimide structure, or on the benzene ring in the O-sulfone benzoic imide structure; and the bond at 6-position is α or β.

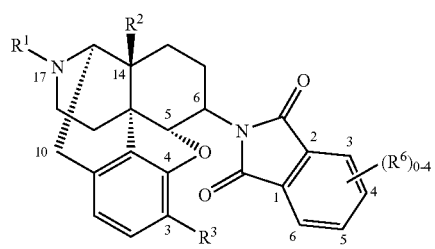

(Ia)

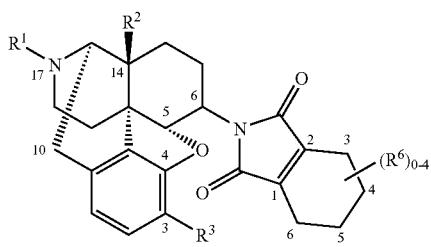

(Ia')

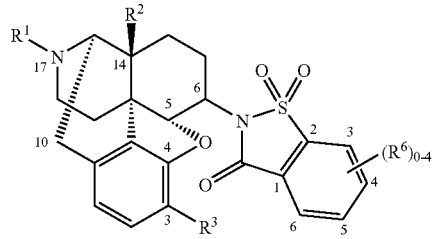

(Ia")

Among the compounds represented by Formula (Ia), the compound wherein $R^1$ is cyclopropylmethyl, $R^2$ and $R^3$ are hydroxy, $R^6$ is 4-fluoro, and the configuration of the bond at the 6-position is β, that is, the compound of the following formula:

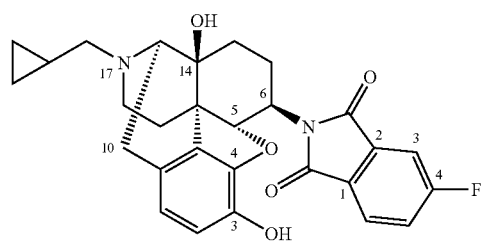

is named N-[17-(cyclopropylmethyl)-4,5α-epoxy-3,14-dihydroxymorphinan-6β-yl]-4-fluorophthalimide.

TABLE 1

| $R^1$ | $R^2$ | $R^3$ | $R^6$ |
|---|---|---|---|
| CPM | OH | OH | (unsubstituted) |
| CPM | OH | OH | 3-F |
| CPM | OH | OH | 4-F |
| CPM | OH | OH | 3,6-F |
| CPM | OH | OH | 4,5-F |
| CPM | OH | OH | 3,4,5,6-F |
| CPM | OH | OH | 3-Cl |
| CPM | OH | OH | 4-Cl |
| CPM | OH | OH | 3,6-Cl |
| CPM | OH | OH | 4,5-Cl |
| CPM | OH | OH | 3-Br |
| CPM | OH | OH | 4-Br |
| CPM | OH | OH | 3,6-Br |
| CPM | OH | OH | 4,5-Br |
| CPM | OH | OH | 3-Me |
| CPM | OH | OH | 4-Me |
| CPM | OH | OH | 3,6-Me |
| CPM | OH | OH | 4,5-Me |
| CPM | OH | OH | 3-OMe |
| CPM | OH | OH | 4-OMe |
| CPM | OH | OH | 3,6-OMe |
| CPM | OH | OH | 4,5-OMe |
| CPM | OH | OH | 3-OH |
| CPM | OH | OH | 4-OH |
| CPM | OH | OH | 3,6-OH |
| CPM | OH | OH | 4,5-OH |
| CPM | OH | OH | 3-$NO_2$ |
| CPM | OH | OH | 4-$NO_2$ |
| CPM | OH | OH | 3,6-$NO_2$ |
| CPM | OH | OH | 4,5-$NO_2$ |
| CPM | OH | OH | 3-$NH_2$ |
| CPM | OH | OH | 4-$NH_2$ |
| CPM | OH | OH | 3,6-$NH_2$ |
| CPM | OH | OH | 4,5-$NH_2$ |
| allyl | OH | OH | (unsubstituted) |
| allyl | OH | OH | 3-F |
| allyl | OH | OH | 4-F |

TABLE 1-continued

| R¹ | R² | R³ | R⁶ |
|---|---|---|---|
| allyl | OH | OH | 3,6-F |
| allyl | OH | OH | 4,5-F |
| allyl | OH | OH | 3,4,5,6-F |
| allyl | OH | OH | 3-Cl |
| allyl | OH | OH | 4-Cl |
| allyl | OH | OH | 3,6-Cl |
| allyl | OH | OH | 4,5-Cl |
| allyl | OH | OH | 3-Br |
| allyl | OH | OH | 4-Br |
| allyl | OH | OH | 3,6-Br |
| allyl | OH | OH | 4,5-Br |
| allyl | OH | OH | 3-Me |
| allyl | OH | OH | 4-Me |
| allyl | OH | OH | 3,6-Me |
| allyl | OH | OH | 4,5-Me |
| allyl | OH | OH | 3-OMe |
| allyl | OH | OH | 4-OMe |
| allyl | OH | OH | 3,6-OMe |
| allyl | OH | OH | 4,5-OMe |
| allyl | OH | OH | 3-OH |
| allyl | OH | OH | 4-OH |
| allyl | OH | OH | 3,6-OH |
| allyl | OH | OH | 4,5-OH |
| allyl | OH | OH | 3-NO₂ |
| allyl | OH | OH | 4-NO₂ |
| allyl | OH | OH | 3,6-NO₂ |
| allyl | OH | OH | 4,5-NO₂ |
| allyl | OH | OH | 3-NH₂ |
| allyl | OH | OH | 4-NH₂ |
| allyl | OH | OH | 3,6-NH₂ |
| allyl | OH | OH | 4,5-NH₂ |
| CPM | H | OH | (unsubstituted) |
| CPM | H | OH | 3-F |
| CPM | H | OH | 4-F |
| CPM | H | OH | 3,6-F |
| CPM | H | OH | 4,5-F |
| CPM | H | OH | 3,4,5,6-F |
| CPM | H | OH | 3-Cl |
| CPM | H | OH | 4-Cl |
| CPM | H | OH | 3,6-Cl |
| CPM | H | OH | 4,5-Cl |
| CPM | H | OH | 3-Br |
| CPM | H | OH | 4-Br |
| CPM | H | OH | 3,6-Br |
| CPM | H | OH | 4,5-Br |
| CPM | H | OH | 3-Me |
| CPM | H | OH | 4-Me |
| CPM | H | OH | 3,6-Me |
| CPM | H | OH | 4,5-Me |
| CPM | H | OH | 3-OMe |
| CPM | H | OH | 4-OMe |
| CPM | H | OH | 3,6-OMe |
| CPM | H | OH | 4,5-OMe |
| CPM | H | OH | 3-OH |
| CPM | H | OH | 4-OH |
| CPM | H | OH | 3,6-OH |
| CPM | H | OH | 4,5-OH |
| CPM | H | OH | 3-NO₂ |
| CPM | H | OH | 4-NO₂ |
| CPM | H | OH | 3,6-NO₂ |
| CPM | H | OH | 4,5-NO₂ |
| CPM | H | OH | 3-NH₂ |
| CPM | H | OH | 4-NH₂ |
| CPM | H | OH | 3,6-NH₂ |
| CPM | H | OH | 4,5-NH₂ |
| allyl | H | OH | (unsubstituted) |
| allyl | H | OH | 3-F |
| allyl | H | OH | 4-F |
| allyl | H | OH | 3,6-F |
| allyl | H | OH | 4,5-F |
| allyl | H | OH | 3,4,5,6-F |
| allyl | H | OH | 3-Cl |
| allyl | H | OH | 4-Cl |
| allyl | H | OH | 3,6-Cl |
| allyl | H | OH | 4,5-Cl |
| allyl | H | OH | 3-Br |
| allyl | H | OH | 4-Br |
| allyl | H | OH | 3,6-Br |
| allyl | H | OH | 4,5-Br |
| allyl | H | OH | 3-Me |
| allyl | H | OH | 4-Me |
| allyl | H | OH | 3,6-Me |
| allyl | H | OH | 4,5-Me |
| allyl | H | OH | 3-OMe |
| allyl | H | OH | 4-OMe |
| allyl | H | OH | 3,6-OMe |
| allyl | H | OH | 4,5-OMe |
| allyl | H | OH | 3-OH |
| allyl | H | OH | 4-OH |
| allyl | H | OH | 3,6-OH |
| allyl | H | OH | 4,5-OH |
| allyl | H | OH | 3-NO₂ |
| allyl | H | OH | 4-NO₂ |
| allyl | H | OH | 3,6-NO₂ |
| allyl | H | OH | 4,5-NO₂ |
| allyl | H | OH | 3-NH₂ |
| allyl | H | OH | 4-NH₂ |
| allyl | H | OH | 3,6-NH₂ |
| allyl | H | OH | 4,5-NH₂ |
| CPM | OAc | OH | (unsubstituted) |
| CPM | OAc | OH | 3-F |
| CPM | OAc | OH | 4-F |
| CPM | OAc | OH | 3,6-F |
| CPM | OAc | OH | 4,5-F |
| CPM | OAc | OH | 3,4,5,6-F |
| CPM | OAc | OH | 3-Cl |
| CPM | OAc | OH | 4-Cl |
| CPM | OAc | OH | 3,6-Cl |
| CPM | OAc | OH | 4,5-Cl |
| CPM | OAc | OH | 3-Br |
| CPM | OAc | OH | 4-Br |
| CPM | OAc | OH | 3,6-Br |
| CPM | OAc | OH | 4,5-Br |
| CPM | OAc | OH | 3-Me |
| CPM | OAc | OH | 4-Me |
| CPM | OAc | OH | 3,6-Me |
| CPM | OAc | OH | 4,5-Me |
| CPM | OAc | OH | 3-OMe |
| CPM | OAc | OH | 4-OMe |
| CPM | OAc | OH | 3,6-OMe |
| CPM | OAc | OH | 4,5-OMe |
| CPM | OAc | OH | 3-OH |
| CPM | OAc | OH | 4-OH |
| CPM | OAc | OH | 3,6-OH |
| CPM | OAc | OH | 4,5-OH |
| CPM | OAc | OH | 3-NO₂ |
| CPM | OAc | OH | 4-NO₂ |
| CPM | OAc | OH | 3,6-NO₂ |
| CPM | OAc | OH | 4,5-NO₂ |
| CPM | OAc | OH | 3-NH₂ |
| CPM | OAc | OH | 4-NH₂ |
| CPM | OAc | OH | 3,6-NH₂ |
| CPM | OAc | OH | 4,5-NH₂ |
| allyl | OAc | OH | (unsubstituted) |
| allyl | OAc | OH | 3-F |
| allyl | OAc | OH | 4-F |
| allyl | OAc | OH | 3,6-F |
| allyl | OAc | OH | 4,5-F |
| allyl | OAc | OH | 3,4,5,6-F |
| allyl | OAc | OH | 3-Cl |
| allyl | OAc | OH | 4-Cl |
| allyl | OAc | OH | 3,6-Cl |
| allyl | OAc | OH | 4,5-Cl |
| allyl | OAc | OH | 3-Br |
| allyl | OAc | OH | 4-Br |
| allyl | OAc | OH | 3,6-Br |
| allyl | OAc | OH | 4,5-Br |
| allyl | OAc | OH | 3-Me |
| allyl | OAc | OH | 4-Me |
| allyl | OAc | OH | 3,6-Me |
| allyl | OAc | OH | 4,5-Me |
| allyl | OAc | OH | 3-OMe |
| allyl | OAc | OH | 4-OMe |
| allyl | OAc | OH | 3,6-OMe |
| allyl | OAc | OH | 4,5-OMe |
| allyl | OAc | OH | 3-OH |

TABLE 1-continued

| R¹ | R² | R³ | R⁶ |
|---|---|---|---|
| allyl | OAc | OH | 4-OH |
| allyl | OAc | OH | 3,6-OH |
| allyl | OAc | OH | 4,5-OH |
| allyl | OAc | OH | 3-NO₂ |
| allyl | OAc | OH | 4-NO₂ |
| allyl | OAc | OH | 3,6-NO₂ |
| allyl | OAc | OH | 4,5-NO₂ |
| allyl | OAc | OH | 3-NH₂ |
| allyl | OAc | OH | 4-NH₂ |
| allyl | OAc | OH | 3,6-NH₂ |
| allyl | OAc | OH | 4,5-NH₂ |

Among the compounds of the Formula (I) according to the present invention, specific examples of those wherein —X— is propenylene (—CH₂—CH═CH—); Y is valence bond; two R⁵s bound to adjacent carbon atoms together form benzo which is unsubstituted or substituted with one or more substituents R⁶(s); R¹⁰, R³ and R¹⁴ are hydrogen; R¹¹ and R¹² are bound to form —O—, that is, those represented by the Formula (Ib) below are shown in Table 2. The number attached to the substituent R⁶ is the position of the substituent on the benzene ring in the isoindole structure, shown in the formula below; and "-" means that the 3-position of the isoindole structure is unsubstituted. The bond at 6-position of the morphinan structure is α or β.

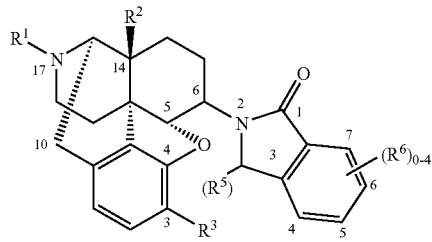

(Ib)

Among the compounds represented by Formula (Ib), the compound wherein R¹ is cyclopropylmethyl, R² and R³ are hydroxy, R⁶ is 6-fluoro, and the configuration of the bond at the 6-position is β, that is, the compound of the following formula:

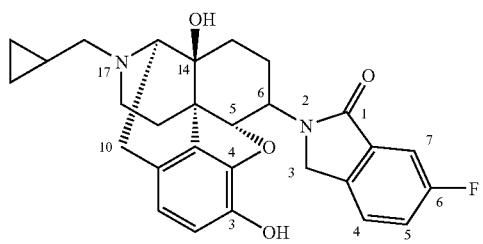

is named 2-[17-(cyclopropylmethyl)-4,5α-epoxy-3,14-dihydroxymorphinan-6β-yl]-6-fluoro-2,3-dihydro-isoindol-1-one.

TABLE 2

| R¹ | R² | R³ | R⁵ | R⁶ |
|---|---|---|---|---|
| CPM | OH | OH | — | (unsubstituted) |
| CPM | OH | OH | — | 4-F |
| CPM | OH | OH | — | 5-F |
| CPM | OH | OH | — | 6-F |
| CPM | OH | OH | — | 7-F |
| CPM | OH | OH | — | 5,6-F |
| CPM | OH | OH | — | 4,5,6,7-F |
| CPM | OH | OH | — | 4-Cl |
| CPM | OH | OH | — | 5-Cl |
| CPM | OH | OH | — | 6-Cl |
| CPM | OH | OH | — | 7-Cl |
| CPM | OH | OH | — | 5,6-Cl |
| CPM | OH | OH | — | 4-Me |
| CPM | OH | OH | — | 5-Me |
| CPM | OH | OH | — | 6-Me |
| CPM | OH | OH | — | 7-Me |
| CPM | OH | OH | — | 5,6-Me |
| CPM | OH | OH | — | 4-OMe |
| CPM | OH | OH | — | 5-OMe |
| CPM | OH | OH | — | 6-OMe |
| CPM | OH | OH | — | 7-OMe |
| CPM | OH | OH | — | 5,6-OMe |
| allyl | OH | OH | — | (unsubstituted) |
| allyl | OH | OH | — | 4-F |
| allyl | OH | OH | — | 5-F |
| allyl | OH | OH | — | 6-F |
| allyl | OH | OH | — | 7-F |
| allyl | OH | OH | — | 5,6-F |
| allyl | OH | OH | — | 4,5,6,7-F |
| allyl | OH | OH | — | 4-Cl |
| allyl | OH | OH | — | 5-Cl |
| allyl | OH | OH | — | 6-Cl |
| allyl | OH | OH | — | 7-Cl |
| allyl | OH | OH | — | 5,6-Cl |
| allyl | OH | OH | — | 4-Me |
| allyl | OH | OH | — | 5-Me |
| allyl | OH | OH | — | 6-Me |
| allyl | OH | OH | — | 7-Me |
| allyl | OH | OH | — | 5,6-Me |
| allyl | OH | OH | — | 4-OMe |
| allyl | OH | OH | — | 5-OMe |
| allyl | OH | OH | — | 6-OMe |
| allyl | OH | OH | — | 7-OMe |
| allyl | OH | OH | — | 5,6-OMe |
| CPM | H | OH | — | (unsubstituted) |
| CPM | H | OH | — | 4-F |
| CPM | H | OH | — | 5-F |
| CPM | H | OH | — | 6-F |
| CPM | H | OH | — | 7-F |
| CPM | H | OH | — | 5,6-F |
| CPM | H | OH | — | 4,5,6,7-F |
| CPM | H | OH | — | 4-Cl |
| CPM | H | OH | — | 5-Cl |
| CPM | H | OH | — | 6-Cl |
| CPM | H | OH | — | 7-Cl |
| CPM | H | OH | — | 5,6-Cl |
| CPM | H | OH | — | 4-Me |
| CPM | H | OH | — | 5-Me |
| CPM | H | OH | — | 6-Me |
| CPM | H | OH | — | 7-Me |
| CPM | H | OH | — | 5,6-Me |
| CPM | H | OH | — | 4-OMe |
| CPM | H | OH | — | 5-OMe |
| CPM | H | OH | — | 6-OMe |
| CPM | H | OH | — | 7-OMe |
| CPM | H | OH | — | 5,6-OMe |
| allyl | H | OH | — | (unsubstituted) |
| allyl | H | OH | — | 4-F |
| allyl | H | OH | — | 5-F |
| allyl | H | OH | — | 6-F |
| allyl | H | OH | — | 7-F |
| allyl | H | OH | — | 5,6-F |
| allyl | H | OH | — | 4,5,6,7-F |
| allyl | H | OH | — | 4-Cl |
| allyl | H | OH | — | 5-Cl |
| allyl | H | OH | — | 6-Cl |
| allyl | H | OH | — | 7-Cl |
| allyl | H | OH | — | 5,6-Cl |
| allyl | H | OH | — | 4-Me |
| allyl | H | OH | — | 5-Me |
| allyl | H | OH | — | 6-Me |

TABLE 2-continued

| R$^1$ | R$^2$ | R$^3$ | R$^5$ | R$^6$ |
|---|---|---|---|---|
| allyl | H | OH | — | 7-Me |
| allyl | H | OH | — | 5,6-Me |
| allyl | H | OH | — | 4-OMe |
| allyl | H | OH | — | 5-OMe |
| allyl | H | OH | — | 6-OMe |
| allyl | H | OH | — | 7-OMe |
| allyl | H | OH | — | 5,6-OMe |
| CPM | OH | OH | OH | (unsubstituted) |
| CPM | OH | OH | OH | 4-F |
| CPM | OH | OH | OH | 5-F |
| CPM | OH | OH | OH | 6-F |
| CPM | OH | OH | OH | 7-F |
| CPM | OH | OH | OH | 5,6-F |
| CPM | OH | OH | OH | 4,5,6,7-F |
| CPM | OH | OH | OH | 4-Cl |
| CPM | OH | OH | OH | 5-Cl |
| CPM | OH | OH | OH | 6-Cl |
| CPM | OH | OH | OH | 7-Cl |
| CPM | OH | OH | OH | 5,6-Cl |
| CPM | OH | OH | OH | 4-Me |
| CPM | OH | OH | OH | 5-Me |
| CPM | OH | OH | OH | 6-Me |
| CPM | OH | OH | OH | 7-Me |
| CPM | OH | OH | OH | 5,6-Me |
| CPM | OH | OH | OH | 4-OMe |
| CPM | OH | OH | OH | 5-OMe |
| CPM | OH | OH | OH | 6-OMe |
| CPM | OH | OH | OH | 7-OMe |
| CPM | OH | OH | OH | 5,6-OMe |
| allyl | OH | OH | OH | (unsubstituted) |
| allyl | OH | OH | OH | 4-F |
| allyl | OH | OH | OH | 5-F |
| allyl | OH | OH | OH | 6-F |
| allyl | OH | OH | OH | 7-F |
| allyl | OH | OH | OH | 5,6-F |
| allyl | OH | OH | OH | 4,5,6,7-F |
| allyl | OH | OH | OH | 4-Cl |
| allyl | OH | OH | OH | 5-Cl |
| allyl | OH | OH | OH | 6-Cl |
| allyl | OH | OH | OH | 7-Cl |
| allyl | OH | OH | OH | 5,6-Cl |
| allyl | OH | OH | OH | 4-Me |
| allyl | OH | OH | OH | 5-Me |
| allyl | OH | OH | OH | 6-Me |
| allyl | OH | OH | OH | 7-Me |
| allyl | OH | OH | OH | 5,6-Me |
| allyl | OH | OH | OH | 4-OMe |
| allyl | OH | OH | OH | 5-OMe |
| allyl | OH | OH | OH | 6-OMe |
| allyl | OH | OH | OH | 7-OMe |
| allyl | OH | OH | OH | 5,6-OMe |
| CPM | H | OH | OH | (unsubstituted) |
| CPM | H | OH | OH | 4-F |
| CPM | H | OH | OH | 5-F |
| CPM | H | OH | OH | 6-F |
| CPM | H | OH | OH | 7-F |
| CPM | H | OH | OH | 5,6-F |
| CPM | H | OH | OH | 4,5,6,7-F |
| CPM | H | OH | OH | 4-Cl |
| CPM | H | OH | OH | 5-Cl |
| CPM | H | OH | OH | 6-Cl |
| CPM | H | OH | OH | 7-Cl |
| CPM | H | OH | OH | 5,6-Cl |
| CPM | H | OH | OH | 4-Me |
| CPM | H | OH | OH | 5-Me |
| CPM | H | OH | OH | 6-Me |
| CPM | H | OH | OH | 7-Me |
| CPM | H | OH | OH | 5,6-Me |
| CPM | H | OH | OH | 4-OMe |
| CPM | H | OH | OH | 5-OMe |
| CPM | H | OH | OH | 6-OMe |
| CPM | H | OH | OH | 7-OMe |
| CPM | H | OH | OH | 5,6-OMe |
| allyl | H | OH | OH | (unsubstituted) |
| allyl | H | OH | OH | 4-F |
| allyl | H | OH | OH | 5-F |
| allyl | H | OH | OH | 6-F |
| allyl | H | OH | OH | 7-F |
| allyl | H | OH | OH | 5,6-F |
| allyl | H | OH | OH | 4,5,6,7-F |
| allyl | H | OH | OH | 4-Cl |
| allyl | H | OH | OH | 5-Cl |
| allyl | H | OH | OH | 6-Cl |
| allyl | H | OH | OH | 7-Cl |
| allyl | H | OH | OH | 5,6-Cl |
| allyl | H | OH | OH | 4-Me |
| allyl | H | OH | OH | 5-Me |
| allyl | H | OH | OH | 6-Me |
| allyl | H | OH | OH | 7-Me |
| allyl | H | OH | OH | 5,6-Me |
| allyl | H | OH | OH | 4-OMe |
| allyl | H | OH | OH | 5-OMe |
| allyl | H | OH | OH | 6-OMe |
| allyl | H | OH | OH | 7-OMe |
| allyl | H | OH | OH | 5,6-OMe |
| CPM | OH | OH | CH$_2$COOMe | (unsubstituted) |
| CPM | OH | OH | CH$_2$COOMe | 4-F |
| CPM | OH | OH | CH$_2$COOMe | 5-F |
| CPM | OH | OH | CH$_2$COOMe | 6-F |
| CPM | OH | OH | CH$_2$COOMe | 7-F |
| CPM | OH | OH | CH$_2$COOMe | 5,6-F |
| CPM | OH | OH | CH$_2$COOMe | 4,5,6,7-F |
| CPM | OH | OH | CH$_2$COOMe | 4-Cl |
| CPM | OH | OH | CH$_2$COOMe | 5-Cl |
| CPM | OH | OH | CH$_2$COOMe | 6-Cl |
| CPM | OH | OH | CH$_2$COOMe | 7-Cl |
| CPM | OH | OH | CH$_2$COOMe | 5,6-Cl |
| CPM | OH | OH | CH$_2$COOMe | 4-Me |
| CPM | OH | OH | CH$_2$COOMe | 5-Me |
| CPM | OH | OH | CH$_2$COOMe | 6-Me |
| CPM | OH | OH | CH$_2$COOMe | 7-Me |
| CPM | OH | OH | CH$_2$COOMe | 5,6-Me |
| CPM | OH | OH | CH$_2$COOMe | 4-OMe |
| CPM | OH | OH | CH$_2$COOMe | 5-OMe |
| CPM | OH | OH | CH$_2$COOMe | 6-OMe |
| CPM | OH | OH | CH$_2$COOMe | 7-OMe |
| CPM | OH | OH | CH$_2$COOMe | 5,6-OMe |
| allyl | OH | OH | CH$_2$COOMe | (unsubstituted) |
| allyl | OH | OH | CH$_2$COOMe | 4-F |
| allyl | OH | OH | CH$_2$COOMe | 5-F |
| allyl | OH | OH | CH$_2$COOMe | 6-F |
| allyl | OH | OH | CH$_2$COOMe | 7-F |
| allyl | OH | OH | CH$_2$COOMe | 5,6-F |
| allyl | OH | OH | CH$_2$COOMe | 4,5,6,7-F |
| allyl | OH | OH | CH$_2$COOMe | 4-Cl |
| allyl | OH | OH | CH$_2$COOMe | 5-Cl |
| allyl | OH | OH | CH$_2$COOMe | 6-Cl |
| allyl | OH | OH | CH$_2$COOMe | 7-Cl |
| allyl | OH | OH | CH$_2$COOMe | 5,6-Cl |
| allyl | OH | OH | CH$_2$COOMe | 4-Me |
| allyl | OH | OH | CH$_2$COOMe | 5-Me |
| allyl | OH | OH | CH$_2$COOMe | 6-Me |
| allyl | OH | OH | CH$_2$COOMe | 7-Me |
| allyl | OH | OH | CH$_2$COOMe | 5,6-Me |
| allyl | OH | OH | CH$_2$COOMe | 4-OMe |
| allyl | OH | OH | CH$_2$COOMe | 5-OMe |
| allyl | OH | OH | CH$_2$COOMe | 6-OMe |
| allyl | OH | OH | CH$_2$COOMe | 7-OMe |
| allyl | OH | OH | CH$_2$COOMe | 5,6-OMe |
| CPM | H | OH | CH$_2$COOMe | (unsubstituted) |
| CPM | H | OH | CH$_2$COOMe | 4-F |
| CPM | H | OH | CH$_2$COOMe | 5-F |
| CPM | H | OH | CH$_2$COOMe | 6-F |
| CPM | H | OH | CH$_2$COOMe | 7-F |
| CPM | H | OH | CH$_2$COOMe | 5,6-F |
| CPM | H | OH | CH$_2$COOMe | 4,5,6,7-F |
| CPM | H | OH | CH$_2$COOMe | 4-Cl |
| CPM | H | OH | CH$_2$COOMe | 5-Cl |
| CPM | H | OH | CH$_2$COOMe | 6-Cl |
| CPM | H | OH | CH$_2$COOMe | 7-Cl |
| CPM | H | OH | CH$_2$COOMe | 5,6-Cl |
| CPM | H | OH | CH$_2$COOMe | 4-Me |
| CPM | H | OH | CH$_2$COOMe | 5-Me |
| CPM | H | OH | CH$_2$COOMe | 6-Me |
| CPM | H | OH | CH$_2$COOMe | 7-Me |
| CPM | H | OH | CH$_2$COOMe | 5,6-Me |

TABLE 2-continued

| $R^1$ | $R^2$ | $R^3$ | $R^5$ | $R^6$ |
|---|---|---|---|---|
| CPM | H | OH | $CH_2COOMe$ | 4-OMe |
| CPM | H | OH | $CH_2COOMe$ | 5-OMe |
| CPM | H | OH | $CH_2COOMe$ | 6-OMe |
| CPM | H | OH | $CH_2COOMe$ | 7-OMe |
| CPM | H | OH | $CH_2COOMe$ | 5,6-OMe |
| allyl | H | OH | $CH_2COOMe$ | (unsubstituted) |
| allyl | H | OH | $CH_2COOMe$ | 4-F |
| allyl | H | OH | $CH_2COOMe$ | 5-F |
| allyl | H | OH | $CH_2COOMe$ | 6-F |
| allyl | H | OH | $CH_2COOMe$ | 7-F |
| allyl | H | OH | $CH_2COOMe$ | 5,6-F |
| allyl | H | OH | $CH_2COOMe$ | 4,5,6,7-F |
| allyl | H | OH | $CH_2COOMe$ | 4-Cl |
| allyl | H | OH | $CH_2COOMe$ | 5-Cl |
| allyl | H | OH | $CH_2COOMe$ | 6-Cl |
| allyl | H | OH | $CH_2COOMe$ | 7-Cl |
| allyl | H | OH | $CH_2COOMe$ | 5,6-Cl |
| allyl | H | OH | $CH_2COOMe$ | 4-Me |
| allyl | H | OH | $CH_2COOMe$ | 5-Me |
| allyl | H | OH | $CH_2COOMe$ | 6-Me |
| allyl | H | OH | $CH_2COOMe$ | 7-Me |
| allyl | H | OH | $CH_2COOMe$ | 5,6-Me |
| allyl | H | OH | $CH_2COOMe$ | 4-OMe |
| allyl | H | OH | $CH_2COOMe$ | 5-OMe |
| allyl | H | OH | $CH_2COOMe$ | 6-OMe |
| allyl | H | OH | $CH_2COOMe$ | 7-OMe |
| allyl | H | OH | $CH_2COOMe$ | 5,6-OMe |

Among the morphinan derivatives having the nitrogen-containing cyclic substituent, represented by Formula (I), or the pharmaceutically acceptable acid addition salts thereof, which are used as an effective ingredient of the antitussive according to the present invention, those wherein both $R^{13}$ and $R^{14}$ are hydrogen, that is, the compounds represented by Formula (Ic) (wherein $R^1$, $R^2$, $R^3$, $R^5$, $R^{10}$, $R^{11}$, $R^{12}$, k, X and Y have the same meanings as described above) or the pharmaceutically acceptable acid addition salts thereof may be, concretely, produced by the method described in International Publication No. WO 04/033457 (European Publication EP1555266).

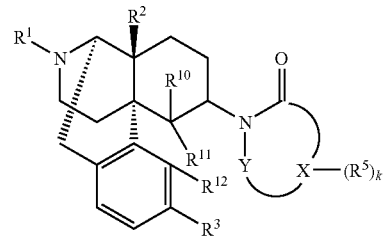

(Ic)

Among the morphinan derivatives having the nitrogen-containing cyclic substituent, represented by Formula (I), or the pharmaceutically acceptable acid addition salts thereof, which are used as an effective ingredient of the antitussive according to the present invention, those wherein both $R^{13}$ and $R^{14}$ are $R^{13'}$ and $R^{14'}$ (wherein $R^{13'}$ and $R^{14'}$ together represent oxo, or $R^{13'}$ is hydrogen and $R^{14'}$ is hydroxy, $C_1$-$C_5$ alkoxy or $C_1$-$C_5$ alkanoyloxy), that is, the compounds represented by Formula (Id) (wherein $R^1$, $R^2$, $R^3$, $R^5$, $R^{10}$, $R^{11}$, $R^{12}$, k, X and Y have the same meanings as described above) may be produced, as shown in Scheme 1, by directly oxidizing the benzyl position of the morphinan derivative having the nitrogen-containing cyclic substituent, represented by Formula (Ic) (wherein $R^1$, $R^2$, $R^3$, $R^5$, $R^{10}$, $R^{11}$, $R^{12}$, k, X and Y have the same meanings as described above) obtained by the method described in International Publication WO 04/033457 (European Publication EP1555266), or by applying the method described in International Publication No. WO 04/033457 (European Publication EP 1555266) to the intermediate represented by Formula (IIb) (wherein $R^1$, $R^2$, $R^3$, $R^{10}$, $R^{11}$, $R^{12}$, $R^{13'}$ and $R^{14'}$ have the same meanings as described above, ••• Q is oxo or dibenzylamino) obtained by oxidizing the benzyl position of the morphinan derivative represented by Formula (IIa) (wherein $R^1$, $R^2$, $R^3$, $R^{10}$, $R^{11}$ and $R^{12}$ have the same meanings as described above, ••• Q is oxo or dibenzylamino). Oxidation of the benzyl position may be attained by directly introducing a hydroxy group or an oxo group, by introducing an oxo group and then reducing it to a hydroxy group, or by introducing a hydroxy group and then oxidizing it to an oxo group. Depending on the type of the substituent, protection and deprotection steps may be added as required.

Scheme 1

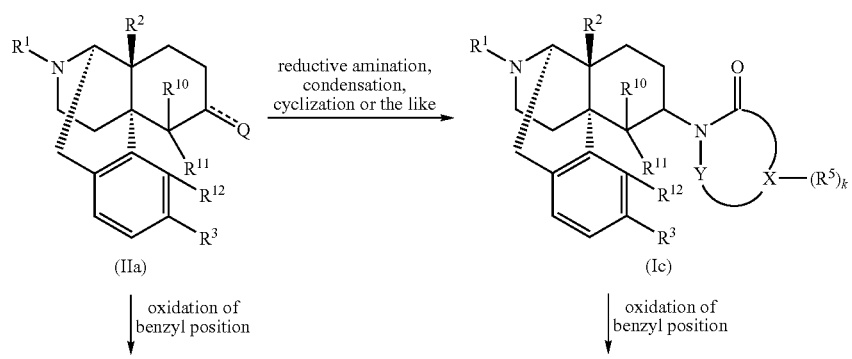

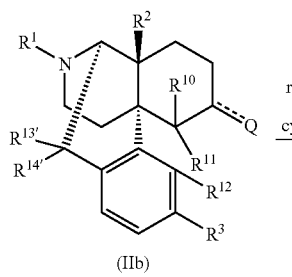 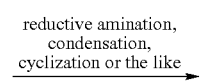 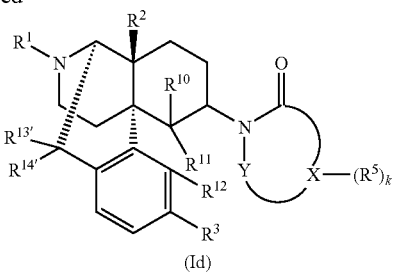

In the oxidation step, any oxidizing agent which may usually be used for the oxidation of the benzyl position may be employed. For introducing a hydroxy group, for example, manganese (III) salts such as manganese (III) acetate; lead compounds such as lead tetraacetate; organic peroxides such as t-butylhydro peroxide and benzoyl peroxide; cerium compounds such as ceric(IV) ammonium nitrate (CAN); and oxygen may be used as the oxidizing agent. Among these oxidizing agents, ceric(IV) ammonium nitrate is useful because α-hydroxy compound may be selectively obtained in some cases. By using an oxidizing agent containing an organic acid such as acetic acid, an alkanoyloxy group such as acetoxy group may be effectively introduced in some cases.

In case of introducing an oxo group, for example, permanganates such as potassium permanganate; manganese compounds such as manganese dioxide; chromium compounds such as chromium oxide and sodium dichromate; selenium compounds such as selenium dioxide; periodates such as sodium periodate; quinones such as DDQ; silver compounds such as silver oxide; cerium compounds such as ceric(IV) ammonium nitrate (CAN); halogens (chlorine, bromine aid iodine); oxygen; and hydrogen peroxide may be employed.

The reaction conditions such as reaction solvent, reaction temperature, reaction time, concentration of the substrate, equivalent ratio of the reactants and the like may be appropriately selected depending on the oxidizing agent employed. For example, in cases where a cerium compound such as ceric(IV) ammonium nitrate (CAN) is used, the desired compound may be obtained with a high yield by reacting 4 equivalents of the oxidizing agent with respect to the substrate at room temperature in acetonitrile/water mixed solvent system.

In cases where an oxo group is reduced to a hydroxy group, any reducing agent which is usually employed in the reduction of carbonyl compounds may be employed, and a hydride reducing agent such as sodium borohydride or lithium aluminium hydride may preferably be employed.

The reaction conditions such as reaction solvent, reaction temperature, reaction time, concentration of the substrate, equivalent ratio of the reactants and the like may be appropriately selected depending on the reducing agent employed. For example, in cases where sodium borohydride is used, the desired compound may be obtained with a high yield by carrying out the reaction in an alcoholic solvent such as methanol at room temperature. In cases where the hydroxy group is formed by the reduction step of the oxo group, β-isomer may be selectively obtained in some cases, opposite to the cases where the hydroxy group is directly formed.

In cases where a hydroxy group is oxidized to an oxo group, any oxidizing agent which is usually employed in oxidizing a hydroxy compound may be employed, and pyridinium chlorochromate (PCC), pyridinium dichromate (PDC), manganese dioxide, DMSO/oxalyl chloride and periodate oxidation products may preferably be employed.

The reaction conditions such as reaction solvent, reaction temperature, reaction time, concentration of the substrate, equivalent ratio of the reactants and the like may be appropriately selected depending on the oxidizing agent employed. For example, in cases where DMSO/oxalyl chloride is used, the desired compound may be obtained with a high yield by carrying out the reaction in a halogen solvent such as dichloromethane at −78° C. to 0° C.

Conversion of the hydroxy compound into the alkoxy compound or alkanoyloxy compound may be attained under the usual etherification or acylation conditions. Conversion of the compound into a salt may be attained by mixing the compound with a pharmaceutically acceptable acid in water or in a various organic solvent, and by conducting concentration to dryness, reprecipitation, recrystallization or the like.

The fact that the morphinan derivatives having the nitrogen-containing cyclic substituent, represented by Formula (I) and the pharmaceutically acceptable acid addition salts thereof are effective for the therapy of coughing may be confirmed by showing inhibitory action against coughing of a guinea pig, which coughing has been induced by administering citric acid to the guinea pig. The inhibitory action against the coughing induced by citric acid administration may be confirmed by the method described in the Examples, but the method is not restricted thereto.

Since the antitussive according to the present invention exhibits potent inhibitory action against the coughing induced by citric acid administration, it is expected that it may be used as a pharmaceutical which may be applied to various disorders accompanied by coughing, for example, various respiratory disorders such as cold (common cold syndrome), acute bronchitis, chronic bronchitis, bronchiectasis, pneumonea, pulmonary tuberculosis, silicosis and silicotic tuberculosis, lung cancer, upper respiratory inflammation (pharyngitis, laryngitis and catarrhal rhinitis), asthmatic bronchitis, bronchial asthma, infantile asthma, (chronic) pulmonary emphysema, pneumoconioses, pulmonary fibrosis, pulmonary suppuration, pleurisy, tonsillitis, cough hives, pertussis and the like; coughing during bronchographic or bronchoscopic examinations or the like.

The antitussive according to the present invention may be administered to mammals (e.g., mouse, rat, hamster, rabbit, cat, dog, bovine, sheep, monkey and human).

When the antitussive according to the present invention is administered, the compound alone may be administered, or the compound may be administered in combination with one or more substances which are used for therapy or prophylaxis of the disease and/or for alleviating or inhibiting the symptom(s). Examples of such substances include nonnarcotic antitussives such as ephedrine, clofedanol, chloperastine, dimemorfan, dextromethorphan, tranilast, noscapine, pentoxyverine, benproperine, fominoben, methylephedrine, tipepidine and the like; narcotic antitussives such as codeine, dihydrocodeine and the like; expectorants such as acetylcysteine, methylcysteine, ethylcysteine, carbocysteine, fudosteine, ambroxol, bromhexine and the like; bronchodilators such as aminophylline, isoprenaline, oxitropium, orciprenaline, clenbuterol, salbutamol, salmeterol, diprophylline, tulobuterol, theophylline, terbutaline, trimetoquiniol, fenoterol, procaterol, beclomethasone, formoterol, mabuterol, methoxyphenamine and the like; nonsteroidal antiinflammatory drugs (NSAIDs) such as aspirin, indomethacin, diclofenac, ibuprofen, acetaminophen, ketoprofen, piroxicam, mefenamic acid, tiaramide, naproxen, loxoprofen, oxaprozin, zaltoprofen, etodolac, meloxicam, lornoxicam, ampiroxicam, celecoxib, rofecoxib, valdecoxib, lumiracoxib, licoferone and the like; antihistamines such as alimemazine, clemastine, chlorpheniramine, diphenylpyraline, diphenhydramine, cyproheptadine, triprolidine, promethazine, homochlorcyclizine, mequitazine and the like; antiallergic drugs such as azelastine, amlexanox, ibtudilast, ebastine, epinastine, emedastine, oxatomide, ozagrel, olopatadine, glycyron, cromoglicate, ketotifen, zafirlukast, suplatast, cetirizine, seratrodast, tazanolast, tranilast, tranexamic acid, fexofenadine, pranlukast, bepotastine, pemirolast, montelukast, ramatroban, repirinast, loratadine and the like; a variety of crude drugs, herbal drugs and the like. It should be noted, however, that these examples are included merely for purposes of illustration and should not be interpreted to limit the scope of the invention.

When clinically using the antitussive according to the present invention, the drug may be the free base or a salt thereof itself, or the drug may be in the form of a mixture with one or more additives such as vehicles, stabilizers, preservatives, buffering agents, solubilizing agents, emulsifiers, diluents, isotonic agents and the like. The drug may be prepared by a usual method appropriately using the carrier(s) for pharmaceuticals. Examples of the formulation for administration include those for oral administration such as tablets, capsules, granules, powders and syrups; those for parenteral administration such as injection solutions, suppositories and liquids; and for topical administration such as ointments, creams and patches. These compositions may be prepared by the methods usually employed.

The therapeutic or prophylactic agent for coughing according to the present invention preferably contains the above-described effective ingredient in a content of 0.00001 to 90% by weight, more preferably 0.0001 to 70% by weight. The dose of administration is appropriately selected depending on the symptom, age, body weight, administration method and the like, and may be: in the case of a formulation for parenteral administration such as injection solution, 0.1 μg to 1 g per day per adult; in case of a formulation for oral administration, 1 μg to 10 g per day per adult; and in case of a formulation for topical administration such as ointments, 0.1 μg to 1 g per day per adult, which dose may be administered in one time or dividedly administered in several times.

EXAMPLES

The present invention will now be described concretely referring to Examples and Comparative Examples.

Compound 1 [N-(17-cyclopropylmethyl-4,5α-epoxy-3,14-dihydroxy-morphinan-6β-yl)-phthalimide], Compound 2 [17-cyclopropylmethyl-4,5α-epoxy-6β-(pyrrolidine-1-yl)-morphinan-3,14-diol.tartaric acid salt], Compound 3 [N-(17-cyclopropylmethyl-4,5α-epoxy-3,14-dihydroxy-morphinan-6β-yl)-3,4,5,6-tetrahydrophthalimide.tartaric acid salt], Compound 4 [2-(7-cyclopropylmethyl-4,5α-epoxy-3,14-dihydroxy-morphinan-6β-yl)-2,3-dihydro-isoindol-1-one-tartaric acid salt] and Compound 5 [N-(17-cyclopropylmethyl-4,5α-epoxy-3,14-dihydroxy-morphinan-6β-yl)-O-sulfonbenzoic acid imide-tartaric acid salt], which were used in Examples 1 and 2 (Compound 1), Example 3 (Compounds 3-5), and Comparative Example 1 (Compounds 2 and 6), were synthesized by the methods described in the Examples 11, 111, 77, 28 and 108 of International Publication WO 2004/033457 (European Publication EP1555266).

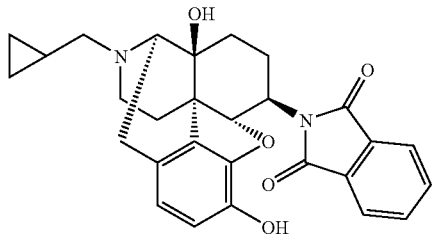

1

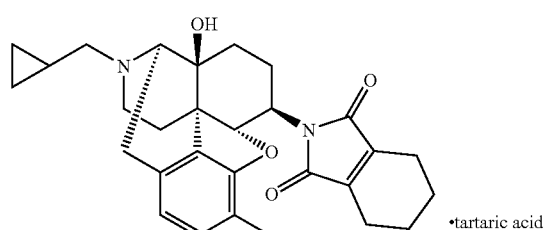

3

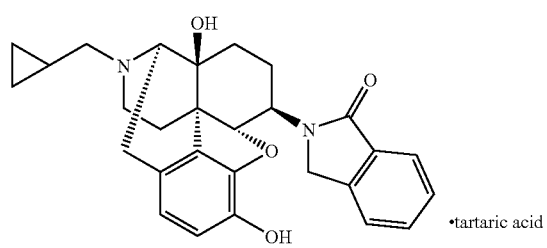

4

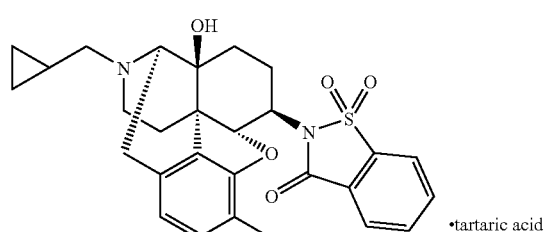

5

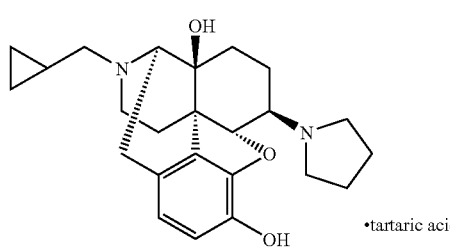

2

Reference Example 1

Synthesis of N-(17-cyclopropylmethyl-4,5α-epoxy-3,14-dihydroxy-morphinan-6β-yl)-maleimide-tartaric acid salt (Compound 6)

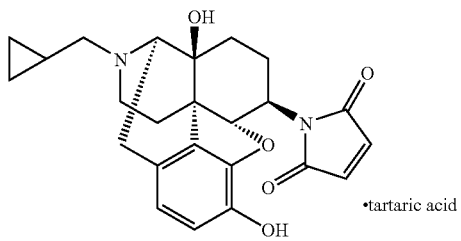

In DMF (30 mL), 800 mg (2.34 mmol) of 6β-naltrexamine was dissolved, and 252 mg (2.57 mmol) of maleic anhydride and 0.48 mL (3.50 mmol) of triethylamine were added thereto, followed by stirring the resulting mixture at room temperature for one and half hours. Thereafter, 0.53 mL (8.18 mmol) of methanesulfonic acid was added and the mixture was stirred at 120° C. for 8 hours.

The reaction solution was left to cool to room temperature) and saturated aqueous sodium hydrogen carbonate solution was added to the reaction mixture, followed by extracting the resulting mixture with ethyl acetate. Organic layers were combined and washed with water and with saturated brine. The resulting mixture was dried over anhydrous magnesium sulfate and concentrated to obtain a crude product. The obtained crude product was purified by silica gel column chromatography to obtain 141 mg (Yield: 14%) of free form of the captioned Compound 6. This product was converted to tartaric acid salt to obtain the captioned compound 6.

$^1$H-NMR (ppm) (400 MHz, CDCl$_3$) 6.70-6.75 (3H, m), 6.61 (1H, d, J=8.0 Hz), 5.02 (1H, d, J=8.3 Hz), 3.8-3.9 (1H, m), 3.08 (1H, d, J=5.6 Hz), 3.04 (1H, d, J=18.3 Hz), 2.6-2.7 (3H, m), 2.3-2.4 (3H, m), 2.12 (1H, dt, J=12.0, 3.6 Hz), 1.4-1.7 (4H, m), 0.8-0.9 (1H, m), 0.5-0.6 (2H, m), 0.1-0.2 (2H, m) (free form)

Mass (EST): 423 (M+1)

Example 1

Effect on Guinea Pig Coughing Models Induced by Citric Acid

A solution of test substance, a solution of positive control substance (codeine phosphate) or the administration solvent was subcutaneously administered to 6 week-old Hartley guinea pigs at a volume of 0.1 mL/100 g. After leaving the guinea pigs to stand for 25 minutes, they were retained in acrylic chambers for cough detection and the chambers were set to a measurement equipment. Thirty minutes after the subcutaneous administration of the test substance, the nebulizer was turned on and 100 mM citric acid solution, a cough inducer, was atomized and sprayed to the face of each guinea pig for a period of 15 minutes (velocity: 50 mm/min). A minipolygraph was used for recording, and the respiratory waveform within the period of 15 minutes was recorded. A signal when a large and acute change of flow rate compared to the respiratory waveform occurred independently was considered as a cough, and marked on the recording sheet. The marking was conducted while recording the respiratory waveform. When a large and continuous amplitude arose by struggling, the amplitude was distinguished by noting that it was caused by struggling. Since some coughings cause just before, and/or between struggling, the recording sheet and the motion of the guinea pig were observed as simultaneously as possible.

The average number of the coughing among the pathosis-induced group by spraying atomized 100 mM citric acid solution was found to be increased to approximately 5 folds (average number of coughing: 17.7 times, n=7) of that among the pathosis-uninduced group sprayed with atomized physiological saline, which was 3.7 times (n=7), so that the establishment of the coughing model was confirmed (p<0.01). When administering the positive control substance, codeine phosphate (10 mg/kg, s.c.), known as an antitussive, the effect for suppressing coughs by approximately 51% was confirmed (p<0.05, n=7). Therefore, it was concluded that antitussive effect can be appropriately evaluated by using the above-described coughing models.

On the other hand, by administering Compound 1 (1 mg/kg, s.c.), the effect for suppressing coughs by approximately 94% in comparison to the cough number of the pathosis-induced group, that is, an antitussive effect, was confirmed (p<0.01, n=7).

Example 2

Evaluation of Compound 1 was conducted in the same manner as in Example 1.

The average number of the coughing among the pathosis-induced group by spraying atomized 100 mM citric acid solution was found to be, increased to approximately 7 folds (average number of coughing: 30.8 times, n=4) of that among the pathosis-uninduced group sprayed with atomized physiological saline, which was 4.3 times (n=3), so that the establishment of the coughing model was confirmed (p<0.05: t-Test). When administering the positive control substance, codeine phosphate (10 mg/kg, s.c.), the effect for suppressing coughs by approximately 37% was confirmed (p<0.05: Welch-Test, n=3). Therefore, it was concluded that antitussive effect can be appropriately evaluated by using the above-described coughing models.

On the other hand, by administering Compound 1 (0.003 mg/kg, s.c.), the effect for suppressing coughs by approximately 50% in comparison to the cough number of the pathosis-induced group, that is, a remarkable antitussive effect, was confirmed (p<0.025: 1 tailed-Shirley-Williams-Test, n=3).

Example 3

Compound 3, 4 and 5 were evaluated in the same manner as in Example 1.

The average number of the coughing among the pathosis-induced group by spraying atomized 100 mM citric acid solution was found to be increased to approximately 8 folds (average number of coughing: 42.0 times, n=3) of that among the pathosis-uninduced group sprayed with atomized physiological saline, which was 5.3 times (n=3), so that the establishment of the coughing model was confirmed (p<0.05: t-Test).

On the other hand, by administering Compound 3, 4 and 5 (0.1 mg/kg, s.c.), the effects for suppressing coughs by approximately 29%, 25% and 28%, respectively, in comparison to the cough number of the pathosis-induced group, that is, remarkable antitussive effects, were confirmed (p<0.05: t-Test, n=3).

Comparative Example 1

As a comparison example, Compound 2 (10 mg/kg, s.c.), and Compound 6 (1 mg/kg, s.c.) were estimated in the same manner as in Example 1. Both of above two compounds showed no decrease in the number of coughs, but rather showed exacerbation, and thus no antitussive effect was observed.

The invention claimed is:

1. A method for suppressing cough comprising administering an effective amount of Compound 1 [N-(17-cyclopropylmethyl-4,5 α-epoxy-3,14-dihydroxy-morphinan-6β-yl)-phthalimide].

* * * * *